(12) United States Patent
Inagi et al.

(10) Patent No.: US 8,034,824 B2
(45) Date of Patent: Oct. 11, 2011

(54) IONTOPHORETIC PREPARATION FOR TREATMENT OF BREAST CANCER AND/OR MASTITIS

(75) Inventors: Toshio Inagi, Fuji (JP); Makoto Kanebako, Fuji (JP); Hiroshi Terada, Tokushima (JP); Kimiko Makino, Bunkyo-ku (JP); Masakazu Toi, Bunkyo-ku (JP)

(73) Assignees: Kowa Co., Ltd., Nagoya-shi (JP); Tokyo University of Science Educational Foundation Administrative Organization, Tokyo (JP)

( * ) Notice: Subject to any disclaimer, the term of this patent is extended or adjusted under 35 U.S.C. 154(b) by 314 days.

(21) Appl. No.: 12/089,804

(22) PCT Filed: Oct. 11, 2006

(86) PCT No.: PCT/JP2006/320320
§ 371 (c)(1),
(2), (4) Date: Apr. 10, 2008

(87) PCT Pub. No.: WO2007/043580
PCT Pub. Date: Apr. 19, 2007

(65) Prior Publication Data
US 2009/0281063 A1    Nov. 12, 2009

(30) Foreign Application Priority Data
Oct. 12, 2005    (JP) .................................. 2005-297565

(51) Int. Cl.
*A61K 31/675*    (2006.01)
*A61K 31/405*    (2006.01)
*A61K 31/513*    (2006.01)
*C07D 209/26*    (2006.01)
*C07D 239/553*    (2006.01)
*C07F 9/6584*    (2006.01)

(52) U.S. Cl. .......... 514/274; 514/420; 514/90; 548/500; 564/13; 544/313

(58) Field of Classification Search .................... 514/90, 514/274
See application file for complete search history.

(56) References Cited

FOREIGN PATENT DOCUMENTS

| JP | 2004 300147 | 10/2004 |
|---|---|---|
| WO | 98 35722 | 8/1998 |
| WO | WO 2004/060322 | * 1/2004 |
| WO | 2004/060322 | 7/2004 |
| WO | 2004 060322 | 7/2004 |
| WO | 2004 105782 | 12/2004 |

OTHER PUBLICATIONS

McCormick (Modulation of Rat Mammary Carcinogenesis by Indomethacin, Cancer research, vol. 45, Apr. 1985, pp. 1803-1808).*
Harrison (Low-Dose Topical 5-Fluorouracil as Effective, Better Tolerated than Standard 5% cream: Presented at AAD, Doctor's Guide, http://docguide.com/news/content.nsf/NewsPrint, pp. 1-2, 2002).*
Jack (Adjuvant Therapy with 5-Fluorouracil for Breast Cancer of Likely Poor Prognosis: 15-Year Results of a Randomized Trial, Clinical Oncology, (1995).*
Powis (Effect of body weight on the pharmacokinetics of cyclophosphamide in breast cancer patients, Cancer Chemotherapy Pharmacology (1987) 20: pp. 219-222).*
Ayumi Denda, "COX-2 and Cancer Prevention", Journal of Clinical and Experimental Medicine, vol. 204, No. 1, 2003, pp. 10-19 (partial translation).
Makoto M. Taketo, "Cyclooxygenase-2 Inhibitors in Tumorigenesis (Part II)", Journal of the National Cancer Institute, vol. 90, No. 21, Nov. 4, 1998, pp. 1609-1620.
Yang Cao, et al.,"Many Actions of Cyclooxygenase-2 in Cellular Dynamics and in Cancer", Journal of Cellular Physiology 190: (2002) pp. 279-286.
Marco E. Turini, et al., "Cyclooxygenase-2: A Therapeutic Target", Annual Review Medicine, 2002, 53, pp. 35-57.
Ayumi Denda, et al., "Increased expression of cyclooxygenase-2 protein during rat hepatocarcinogenesis caused by a choline-deficient, I-amino acid-defined diet and chemopreventive efficacy of a specific inhibitor, nimesulide", Carcinogenesis vol. 23, No. 2, 2002, pp. 245-256.
Yoshiko Ohtaka, et al., "Mastitis and Breast-feeding", Perinatal Medicine, vol. 34, No. 9, Sep. 2004, pp. 1443-1445.
Yokohama Igaku, Journal of Yokohama Medical Association, 44, 1993, pp. 487-494.
Dermatology and Venereology, v(2), 65, 1951.

* cited by examiner

*Primary Examiner* — San-Ming Hui
*Assistant Examiner* — Kathrien Cruz
(74) *Attorney, Agent, or Firm* — Oblon, Spivak, McClelland, Maier & Neustadt, L.L.P.

(57) ABSTRACT

The present invention is to provide means to treat breast cancer and/or mastitis by topically administering a non-steroidal antiinflammatory analgetic agent and/or an anticancer agent and allowing them efficiently to arrive into the mammary gland. The present invention provides an iontophoretic preparation for treating breast cancer and/or mastitis which contains a non-steroidal antiinflammatory analgetic agent and/or an anticancer agent as an active ingredient and has a donor to be applied on a nipple part for topical administration of the active ingredient from the nipple part to the mammary gland by application of electric potential.

10 Claims, 2 Drawing Sheets

US 8,034,824 B2

IONTOPHORETIC PREPARATION FOR TREATMENT OF BREAST CANCER AND/OR MASTITIS

CROSS-REFERENCE TO RELATED APPLICATIONS

This application is a 371 application of PCT/JP2006/320320 filed Oct. 11, 2006 and claims the benefit of JP 2005-297565 filed Oct. 12, 2005.

TECHNICAL FIELD

The present invention relates to an iontophoretic preparation for the treatment of breast cancer and/or mastitis.

BACKGROUND ART

Breast cancer is a cancer which occurs in mammary gland tissues and is classified into lobular carcinoma arising from acinus and breast ductal carcinoma arising from breast ducts. The state of cancer limited within lobules or breast ducts and not disseminating to surrounding tissue is called noninfiltrating cancer whereas the state in which cancer cells proliferating in breast ducts destroy basement membrane and develop metastasis to the neighboring tissues is called infiltrating cancer. As a treatment method for breast cancer, adjuvant chemotherapy is common, in which an anticancer agent is administered by instillation after surgery operation for excising affected parts or without surgery operation. However, many of anticancer agents have problems that they may cause side effects such as nausea, loss of appetite and alopecia when administered by instillation.

Meanwhile, it has been reported that activities of cyclooxygenase-1 (COX-1) and cyclooxygenase-2 (COX-2) increase upon the development of breast cancer (Non-patent Documents 1 to 5). Furthermore, it is known that non-steroidal antiinflammatory analgetic agents are effective for inhibiting COX-1 and COX-2.

Mastitis is classified into stagnation mastitis and acute suppurative mastitis. Stagnation mastitis develops just after the puerperium in the state that milk stagnates within breast ducts. On the other hand, acute suppurative mastitis develops by infection of bacteria such as *staphylococcus, Escherichia coli* and *streptococcus*. Of these, treatment with an antiinflammatory analgetic agent is performed for acute suppurative mastitis (Non-patent Document 6).

However, there has been a problem that non-steroidal antiinflammatory analgetic and/or anticancer agents cannot be administered topically since breast cancer and mastitis occur or develop within the breast.

As attempts to treat breast diseases such as breast cancer by topical administration of a medicinal agent, methods of percutaneously administering adriamycin, danazol or progesterone to the breast have been reported (Non-patent Document 7, 8 and Patent Document 1).

[Patent Document 1] WO2004/060322 (Description) [Non-patent Document 1] Igaku no Ayumi (Journal of Clinical and Experimental Medicine), 204 (1), 10-19, 2003
[Non-patent Document 2] Journal of the National Cancer Institute, 90 (21), 1609-1620, 1998
[Non-patent Document 3] Journal of Cellular Physiology, 190, 279-286, 2002
[Non-patent Document 4] Annual Reviews Medicine, 53, 35-57, 2002
[Non-patent Document 5] Carcinogenesis, 23(2), 245-256, 2002
[Non-patent Document 6] Shusanki Igaku (Perinatal Medicine), 34 (9), 1443-1445, 2004
[Non-patent Document 7] Yokohama Igaku (Journal of Yokohama Medical Association), 44, 487-494, 1993
[Non-patent Document 8] Dermatology and Venereology, V(2), 65, 1951

DISCLOSURE OF THE INVENTION

Problems to be Solved by the Invention

When non-steroidal antiinflammatory analgetic agents and/or anticancer agents were administered by conventional topical administration means, their delivery rate to the location of breast cancer or affected parts of mastitis is extremely low and accordingly, such an approach has not come into practical use.

Therefore, an object of the present invention is to provide means to treat breast cancer and/or mastitis by topically administering a non-steroidal antiinflammatory analgetic agent and/or an anticancer agent and allowing them efficiently to arrive into the mammary gland.

Means for Solving the problems

The present inventors have directed attention to iontophoresis known as an enhancing method of percutaneous absorption and conducted studies thereon, and consequently, have found that when a donor of an iontophoretic preparation which contains a non-steroidal antiinflammatory analgetic agent and/or an anticancer agent is applied on a nipple part and to which electric potential is applied, the delivery rate of these active ingredients to the mammary gland is drastically enhanced as compared with a case in which the donor is applied on normal skin such as breast parts and electric potential is applied, and therefore such an approach is useful as a method to treat breast cancer and/or mastitis by topical administration. Thus, the present invention has been accomplished on the basis of this finding.

That is, the present invention provides an iontophoretic preparation for treating breast cancer and/or mastitis which contains a non-steroidal antiinflammatory analgetic agent and/or an anticancer agent as an active ingredient and has a donor to be applied on a nipple part for topical administration of the active ingredient from the nipple part to the mammary gland by application of electric potential.

In addition, the present invention also provides an iontophoretic therapeutic method comprising applying a donor which contains a non-steroidal antiinflammatory analgetic agent and/or an anticancer agent as an active ingredient on a nipple part and topically administrating the active ingredient from the nipple to the mammary gland by application of electric potential.

Further, the present invention provides use of a non-steroidal antiinflammatory analgetic agent and/or an anticancer agent for the production of an iontophoretic preparation for treating breast cancer and/or mastitis which contains a donor to be applied on a nipple part for topical administration of the active ingredient from the nipple to the mammary gland by application of electric potential.

Effects of the Invention

The present invention enables non-steroidal antiinflammatory analgetic agents and/or anticancer agents which are active ingredients to be specifically absorbed in the mammary gland, and accordingly, treatment of breast cancer and/or mastitis becomes possible with lower doses than conventional methods, thereby reducing side effects.

DESCRIPTION OF SYMBOLS

Figure 1:
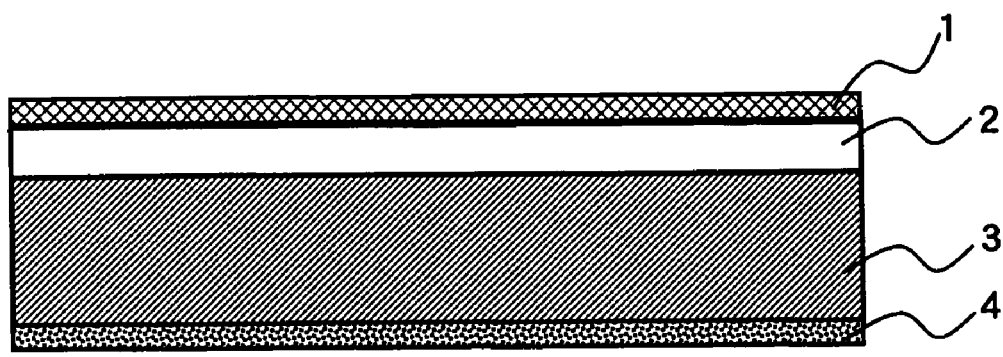
FIG. 1 shows a schematic sectional view illustrating an iontophoretic preparation for breast cancer and/or mastitis treatment of the present invention.

1 Support
2 Electrode
3 Pad
4 Liner

BEST MODE FOR CARRYING OUT THE INVENTION

With the iontophoretic preparation for breast cancer and/or mastitis treatment of the present invention, a donor is applied to a nipple part and an active ingredient is topically administrated from the nipple part into the mammary gland by application of electric potential. It has been utterly unexpected that permeability is enhanced remarkably in administration from the nipple part by application of electric potential as compared with administration from normal skin such as breasts.

Examples of the non-steroidal antiinflammatory analgetic agent which is the active ingredient of the therapeutic agent for breast cancer and/or mastitis of the present invention include indomethacin, acemetacin, salicylic acid, sodium salicylate, aspirin, acetaminophen, diclofenac sodium, anfenac sodium, ibuprofen, sulindac, naproxen, ketoprofen, flufenamic acid, ibufenac, fenbufen, alclofenac, phenylbutazone, mefenamic acid, benzadac, piroxicam, flurbiprofen, pentazocine, buprenorphine hydrochloride, butorphanol tartrate, celecoxib, rofecoxib, valdecoxib, etoricoxib, Lumiracoxib, parecoxib Na, etodolac, NS-398 and meloxicam. Of these, indomethacin and celecoxib are preferable at a point of absorption efficiency from the nipple part to the mammary gland, and indomethacin is particularly preferable.

Examples of the anticancer agent include alkylating agents such as ifosfamide and cyclophosphamide; platinum compounds such as carboplatin, cisplatin, nedaplatin and oxaliplatin; vegetable anticancer agents such as irinotecan hydrochloride, etoposide, docetaxel hydrate, vincristine sulfate, vinblastine sulfate, paclitaxel and vinorelbine ditartrate; hormones such as tamoxifen citrate, fadrozole hydrochloride hydrate, flutamide and medroxyprogesterone acetate; anticancerous antibiotics such as doxorubicin hydrochloride, idarubicin hydrochloride, zinostatin stimalamer, daunorubicin hydrochloride, bleomycin hydrochloride, epirubicin hydrochloride, mitoxantrone hydrochloride, pirarubicin hydrochloride and mitomycin C; antimetabolites such as carmofur, cytarabine, doxifluridine, hydroxycarbamide, methotrexate, mercaptopurine, gemcitabine hydrochloride, fluorouracil and capecitabine; linear surfactin having a lactone type cyclohepta peptide structure and monoclonal antibodies such as trastuzumab. Of these, alkylating agents such as cyclophosphamide and antimetabolites such as fluorouracil are preferable at a point of absorption efficiency from the nipple part to the mammary gland, and cyclophosphamide and fluorouracil (in particular, 5-FU) are particularly preferable.

When the donor of the iontophoretic preparation of the present inventor is applied on the nipple part and an active ingredient is topically administered from the nipple part to the mammary gland by application of electric potential, migration of an anticancer agent and a non-steroidal antiinflammatory agent from the nipple part to the mammary gland is drastically enhanced as compared with application of electric potential on the normal skin, as demonstrated in the aftermentioned Examples, although the degree of migration properties are different depending upon the kind of drugs. The transfer properties are particularly remarkable in indomethacin, cyclophosphamide and fluorouracil.

An iontophoretic preparation usually consists of a donor and a receptor, but as for the iontophoretic preparation of the present invention for breast cancer and/or mastitis treatment, at least the donor is applied on the nipple part. The donor may have an electrode and a pad containing the aforementioned active ingredient, and the pad containing the active ingredient may contain an electrolyte. The iontophoretic preparation generally consists of a power supply, an anode (an electrode and a pad) and a cathode (an electrode and a pad). Examples of the shape of electrodes include a pairing structure in which the anode and the cathode make an opposing pair; and a surrounding structure in which the anode and/or the cathode is located inside while the cathode and/or the anode is located outside (Biological Pharmaceutical Bulletin, 26(4), 518-522, 2003). Here, in an anionic drug, the cathode is used as a donor, and in a cationic drug, the anode is used as a donor, and as for a nonionic drug, the anode is used as a donor using a principle of electroosmosis (Biological Pharmaceutical Bulletin, 24, 278-283, 2001; Biological Pharmaceutical Bulletin, 24, 671-677, 2001; and Pharmaceutical Research, 18, 1701-1708, 2001).

Firstly, the donor is described. The donor basically consists of a support 1, an electrode 2, a pad 3 containing an active ingredient and a liner 4 as illustrated in FIG. 1. Examples of the support include cotton, polyester, rayon, nylon, polyolefin, polyethylene, vinylon, acetate, polypropylene and polyurethane. Examples of the electrode include aluminum (including aluminum oxide), stainless steel, gold, silver, silver chloride, platinum and platinum black. The pad containing an active ingredient contains an active ingredient, a solvent, an adhesive base material and may optionally contain an electrolyte as required. Examples of the liner include plastic liners such as polyethylene and polypropylene, cellulosic liners and one having a silicone release agent coated on the surface of the above liner and a paper sheet.

Examples of the solvent constituting the pad of the present invention include water; polyhydric alcohols such as ethyleneglycol, diethylene glycol, triethylene glycol, ethylene glycol monoethyl ether, ethylene glycol monobutyl ether, diethylene glycol monomethyl ether, polyethylene glycol, propylene glycol, dipropylene glycol, 1,3-butylene glycol, dipropylene glycol polyethylene glycol, 2-ethyl-1,3-hexane diol, polypropylene glycol 2000, polypropylene glycol, (concentrated) glycerin, batyl alcohol, pentaerythritol and D-sorbitol liquid; alcohols such as ethanol, isopropanol, benzyl alcohol, lauryl alcohol, cetanol, stearyl alcohol, oleyl alcohol and lanolin alcohol; diisopropyl adipate, triacetin, diisopropyl sebacate, triisooctane acid and esters such as triglycerides of medium chain fatty acids having 6 to 12 carbon atoms; ketones such as crotamiton and one kind of these or two or more kinds of these in combination can be used.

Examples of the adhesive base material constituting the pad of the present invention include water-soluble adhesive base materials such as polyacrylic acid, sodium polyacrylate, partially neutralized polyacrylic acid and N-vinyl acetamide-acrylic acid co-polymers, and hydrophobic adhesive base materials such as ester gums, alicyclic saturated hydrocarbon resins, aliphatic hydrocarbon resins, polybutene and rosin. One kind of these or two or more kinds of these in combination can be used.

Sodium chloride, potassium chloride, sodium bromide, potassium bromide, calcium chloride, calcium bromide and the like may be used as an electrolyte constituting the pad of the present invention.

Base materials, thickening agents, preservatives, pH adjusters, oil ingredients, flavoring agents, stabilizers, surfactants, curing agents and chemical enhancers can be also added to the pad.

Examples of the base material include sodium alginate, ethyl cellulose, carrageenan, carmellose sodium, agar, xanthan gum, gelatine, kaolin, bentonite, montmorillonite, zinc oxide, titanium oxide, silicic anhydride, D-sorbitol, talc, terpene resins, hydroxypropylcellulose and hydroxypropylmethylcellulose.

Examples of the thickening agent include carboxyvinyl polymer, urea, polyvinyl alcohol and sodium metaphosphate.

Examples of the preservative include phenolic substances such as methyl parahydroxybenzoate, phenol and cresol, neutral substances such as chlorobutanol and phenylethyl alcohol, invert soaps such as benzalkonium chloride and benzethonium chloride, and acidic substances such as benzoic acid, sorbic acid, dehydro acid and salicylic acid.

Examples of the pH adjuster include citric acid, sodium citrate, hydrochloric acid, glycine, succinic acid, acetic acid, diisopropanolamine, tartaric acid, potassium hydroxide, sodium hydroxide, lactic acid, boric acid, malic acid and phosphoric acid.

Examples of the oil ingredient include olive oil, camellia oil, castor oil, safflower oil, sunflower oil, sasanqua oil, soybean oil, cottonseed oil, sesame oil, coconut oil, palm oil and clove oil.

Examples of the flavoring agent include fennel oil, cinnamon oil, clove oil and peppermint oil.

Examples of the stabilizer include anti-oxidants such as vitamin E and butylhydroxyanisol, reducing agents such as ascorbic acid, sodium hydrogensulfite and sodium thiosulfate, and synergistic agents such as sodium citrate, sodium tartrate, lecithin and EDTA.

Examples of the surfactant include anionic surfactants such as calcium stearate, magnesium stearate and sodium lauryl sulfate, cationic surfactants such as benzalkonium chloride, benzethonium chloride and cetylpyridinium chloride, nonionic surfactants such as glyceryl monostearate, sugar fatty acid esters, polyoxyethylene hydrogenated castor oil and polyoxyethylene sorbitan fatty acid esters.

Examples of the curing agent include dried aluminum hydroxide gel, aluminum magnesium hydroxide, magnesium aluminosilicate, magnesium aluminometasilicate, synthetic hydrotalcite and dihydroxyaluminum aminoacetate.

Examples of the chemical enhancers include nonionic surfactants such as monostearic acid glyceryl and sugar fatty acid esters, water-soluble polymer compounds such as carboxylic acids, aromatic carboxylic acid compounds such as salicylic acid and the derivatives thereof, aliphatic carboxylic acid compounds such as capric acid and oleic acid, terpenes such as L-menthol, esters such as isopropyl myristate and diethyl sebacate, bile salt, hydrogenated lanoline and azone.

The content of the active ingredient in the pad is preferably 0.01 to 20 mass %, more preferably 0.1 to 10 mass % from a point of migration of the active ingredient from the nipple to the mammary gland.

In the meantime, the receptor of the iontophoretic preparation for breast cancer and/or mastitis treatment of the present invention is basically constituted of a support 1, an electrode 2, a pad 3 and a liner 4 as shown in FIG. 1 as well. The support, the electrode and the liner are made of materials similar to those of a donor, and the pad does not contain an active ingredient but contains an electrolyte.

Furthermore, the preparation may form a surrounding structure in which a power supply, a donor and a receptor are incorporated as in WO98/35722, or may form a pair structure in which a power supply, a donor and a receptor are separated.

Figure 2:
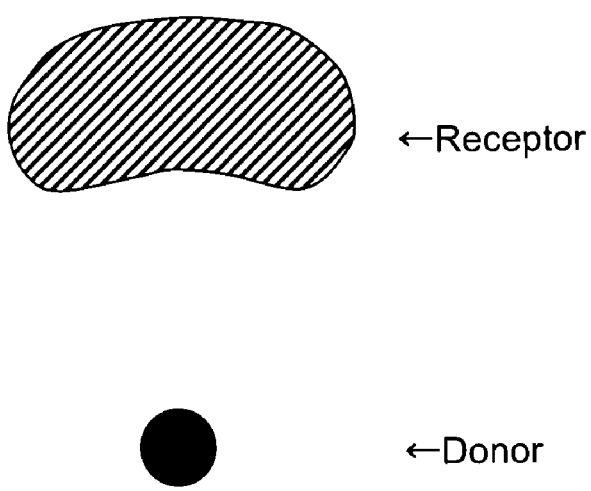
FIG. 2 illustrates an example of the shape of the donor and the receptor of an iontophoretic preparation for breast cancer and/or mastitis treatment of the present invention.
Figure 3:
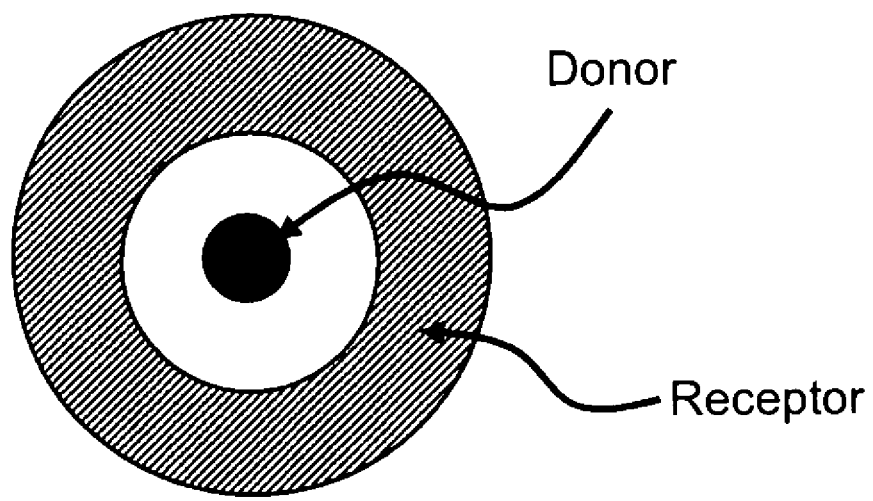
FIG. 3 illustrates an example of the shape of the donor and the receptor of an iontophoretic preparation for breast cancer and/or mastitis treatment of the present invention

It is preferable in present invention to apply a donor to the nipple part and place a receptor on the breast part at a point of allowing a non-steroidal antiinflammatory analgetic agent and/or an anticancer agent to selectively and efficiently migrate from the nipple to the mammary gland. In this case, it is preferable that the donor is a donor having a size to cover up the whole nipple part. On the other hand, it is preferable that the receptor is a receptor having a size to wrap up at least the affected area of the breast. The shape of the donor is not limited, but a circle or an oval form is preferable in that it may cover the nipple, and the shape of the receptor is preferably a circle, an oval form, a disk or an oval disk in that it may cover at least the affected area of the breast (FIGS. 2 and 3). The receptor particularly preferably has a shape which covers up the whole breast except the nipple part, for example, forms like a disk or an oval disk (FIG. 3).

The iontophoretic preparation for breast cancer and/or mastitis treatment of the present invention has an electrode and a pad containing an active ingredient as a donor and has an electrode and a pad containing an electrolyte as a receptor, and when the active ingredient is an anionic drug such as indomethacin, for example, an electronic flow from the donor (cathode) to the receptor (anode) occurs by applying the donor onto the nipple part and the receptor onto the breast part and applying an electric potential and this flow allows indomethacin in the donor to absorb into the mammary gland. In the case of a nonionic drug such as carmofur or fluorouracil, the drug is absorbed into the mammary gland through an aquatic flow associated with the transfer of the other cations from the donor (anode) to the receptor (cathode).

EXAMPLES

Hereinbelow, the present invention will next be described in more detail by way of examples, but the present invention is not limited to these examples by any means.

Example 1

A permeation experiment (in vitro) through a skin excised from a beagle by iontophoresis was performed using a indomethacin-containing solution.

As for the excised skin, the abdominal skin of a beagle (male, 3-year old) was subjected to dehairing treatment and then a skin area containing a nipple and a skin area not containing a nipple were excised and used. Idomethine Kowa Sol (produced by Kowa Co., Ltd., lot number QF45) was used as a donor solution just as it was. A mixed solvent of macrogol 400 and saline (mass mixing rate; macrogol 400/normal saline solution=6:4) was used as a receptor solution. Two kinds of the excised skin were attached on Franz cells with the surface thereof on the donor side and the cells were filled with 1 mL of the donor solution and 19 mL of the receptor solution. A silver chloride electrode was inserted in the donor (cathode) side whereas a silver electrode was inserted in the receptor (anode) side so that they might be sufficient contact with the liquid and an electric potential at 0 or 3V was applied by a DC voltage current generator for 100 minutes. When 20, 40, 60, 80 and 100 minutes passed after the start of the application of electric potential, 1 mL of the receptor liquid was sampled from a sampling port of the receptor side and 1 mL of a new receptor liquid was supplemented. The indomethacin concentration in the sampled receptor liquid was measured by HPLC method. Here, since the skin including the nipple (0.196 cm$^2$) included the skin (0.589 cm$^2$) other than the nipple, the permeated amount was corrected based on the whole permeation area (0.785 cm$^2$) to indicate a value only through the nipple part.

The time change course of the accumulated permeated amount of indomethacin and the increase rate after 100 minutes are shown in Table 1. The permeability of indomethacin through normal skin increased only by about 2 times when electric potential was applied at 3V whereas the permeability of indomethacin from the nipple increased by about 10 times than that through normal skin without application of electric potential and by about 17 times when electric potential was applied at 3V.

Two kinds of the excised skin were attached on Franz cells with the surface thereof on the donor side and the cells were filled with 3 mL of the donor solution and 31 mL of the receptor solution. Aluminum foil was attached to donor (anode) side and receptor (cathode) side electrodes and the electrodes were inserted so that they might be sufficient contact with the liquid and an electric potential at 0 or 0.1 mA/cm$^2$ was applied by a DC voltage current generator for 180 minutes. When 30, 60, 90, 120, 150 and 180 minutes passed after the start of the application of electric potential, 1 mL of the receptor liquid was sampled from a sampling orifice of the receptor side and 1 mL of a new receptor liquid was supplemented. The cyclophosphamide concentration in the sampled receptor liquid was measured by HPLC method. Here, since the skin including the nipple (0.629 cm$^2$) included the skin (2.511 cm$^2$) other than the nipple, permeated amount was

TABLE 1

Table for permeated amount (μg/cm$^2$) of indomethacin and increase rate thereof

| Skin | Condition | Time (min) | | | | | Increase rate of permeated amount after 100 minutes with respect to normal skin without application of electric potential |
|---|---|---|---|---|---|---|---|
| | | 20 | 40 | 60 | 80 | 100 | |
| Normal skin | No application of electric potential | 0.33 | 0.45 | 0.77 | 1.27 | 1.37 | |
| | Application of electric potential | 0.57 | 0.78 | 1.38 | 2.03 | 2.52 | 1.84 |
| Nipple skin | No application of electric potential | ND | ND | 2.91 | 8.69 | 13.95 | 10.18 |
| | Application of electric potential | 2.85 | 7.27 | 9.07 | 10.42 | 23.65 | 17.26 |

Example 2

A permeation experiment (in vitro) through a skin excised from a beagle by iontophoresis was performed using a cyclophosphamide-containing solution.

As for the excised skin, the skin on the abdomen of a beagle (male, 3-year old) was subjected to dehairing treatment and then a skin area containing a nipple and a skin area not containing a nipple were excised and used. A buffer solution containing 25 mM cyclophosphamide (25 mM HEPES buffer containing 133 mM NaCl, pH 3) was used as a donor solution. A 25 mM HEPES buffer containing 133 mM NaCl (pH 3) was used as a receptor solution.

corrected based on the whole permeation area (3.14 cm$^2$) to indicate a value only through the nipple part.

The time change course of the accumulated permeated amount of cyclophosphamide and the increase rate after 180 minutes are shown in Table 2. The permeability of cyclophosphamide through normal skin hardly changed even when an electric potential was applied (at 0.1 mA/cm$^2$) and the permeability of cyclophosphamide from the nipple was not enhanced as compared with the permeability through normal skin. Nevertheless, the permeability from the nipple when an electric potential (at 0.1 mA/cm$^2$) increased by about 7.1 times as compared with the permeability through normal skin without application of electric potential.

TABLE 2

Table for permeated amount (μg/cm$^2$) of cyclophosphamide and increase rate thereof

| Skin | Condition | Time (min) | | | | | | | Increase rate of permeated amount after 180 minutes with respect to normal skin without application of electric potential |
|---|---|---|---|---|---|---|---|---|---|
| | | 0 | 30 | 60 | 90 | 120 | 150 | 180 | |
| Normal skin | No application of electric potential | 0.0 | 13.3 | 14.4 | 15.0 | 15.5 | 17.2 | 17.4 | |
| | Application of electric potential | 0.0 | 13.4 | 13.9 | 13.7 | 16.2 | 16.3 | 16.2 | 0.9 |
| Nipple skin | No application of electric potential | 0.0 | 24.9 | 2.0 | 6.9 | 20.2 | 1.4 | 6.9 | 0.4 |
| | Application of electric potential | 0.0 | 34.3 | 123.2 | 125.3 | 121.4 | 120.4 | 123.1 | 7.1 |

Example 3

A permeation experiment (in vitro) through a skin excised from a beagle by iontophoresis was performed using a 5-fluorouracil-containing solution.

As for the excised skin, the skin on the abdomen of a beagle (male, 3-year old) was subjected to dehairing treatment and then a skin area containing a nipple and a skin area not containing a nipple were excised and used. A buffer solution containing 1% 5-fluorouracil (25 mM HEPES buffer containing 133 mM NaCl, pH 8.5) was used as a donor solution. A normal saline solution was used as a receptor solution.

Two kinds of the excised skin were attached on Franz cells with the surface thereof on the donor side and the cells were filled with 1 mL of the donor solution and 19 mL of the receptor solution. Aluminum foil was attached to donor (cathode) side and receptor (anode) side electrodes and the electrodes were inserted so that they might be sufficient contact with the liquid and an electric potential at 0 or 3 V was applied by a DC voltage current generator for 360 minutes. When 60, 120, 180, 240, 300 and 360 minutes passed after the start of the application of electric potential, 1 mL of the receptor liquid was sampled from a sampling orifice of the receptor side and 1 mL of a new receptor liquid was supplemented. The 5-fluorouracil concentration in the sampled receptor liquid was measured by HPLC method. Here, since the skin including the nipple (0.385 cm$^2$) included the skin (0.4 cm$^2$) other than the nipple, permeated amount was corrected based on the whole permeation area (0.785 cm$^2$) to indicate a value only through the nipple part.

TABLE 3

Table for permeated amount (μg/cm$^2$) of 5-fluorouracil and increase rate thereof

| Skin | Condition | Time (min) | | | | | | Increase rate of permeated amount after 360 minutes with respect to normal skin without application of electric potential |
|---|---|---|---|---|---|---|---|---|
| | | 60 | 120 | 180 | 240 | 300 | 360 | |
| Normal skin | No application of electric potential | 0.0 | 0.0 | 0.0 | 0.0 | 0.1 | 0.1 | |
| | Application of electric potential | 1.3 | 11.7 | 44.4 | 121.5 | 264.9 | 480.3 | 3430.7 |
| Nipple skin | No application of electric potential | 0.0 | 0.2 | 0.7 | 1.6 | 3.0 | 5.6 | 39.7 |
| | Application of electric potential | 17.6 | 151.7 | 383.3 | 676.3 | 1032.3 | 1391.3 | 9937.8 |

The time change course of the accumulated permeated amount of 5-fluorouracil and the increase rate after 360 minutes are shown in Table 3. The permeability of 5-fluorouracil through normal skin increased by about 3000 times when an electric potential was applied (at 3V) and the permeability of 5-fluorouracil from the nipple increased by about 40 times compared with the permeability without application of electric potential, and increased by about 10000 times than that through normal skin when electric potential applied (at 3V).

Example 4

One (1) g of polyvinyl alcohol (partially saponified substance) was added to 40 g of a normal saline solution, heated to 50° C. and dissolved. After cooling to room temperature, 0.1 g of sodium edetate and 1.3 g of tartaric acid were added and dissolved, and then 20 g of concentrated glycerin was added (aqueous phase). Separately, 3.5 g of carmellose sodium, 5 g of partially neutralized polyacrylic acid (NP-700), 5 g of partially neutralized polyacrylic acid (NP-800) and 0.2 g of dihydroxy aluminum acetate were added to 20 g of macrogol 400, and uniformly suspended (oily phase). The oily phase was added to the aqueous phase and, furthermore, a normal saline solution was added thereto to adjust the total amount to 100 g. This mixture was uniformly kneaded with a kneader and extended with an extender to a thickness of 1 mm and thus pads of the composition of Table 4 were prepared.

TABLE 4

| Ingredient | Content (g) |
|---|---|
| Polyvinyl alcohol (partially saponified substance) | 1 |
| Sodium edetate | 0.1 |
| Concentrated glycerin | 20 |
| Carmellose sodium | 3.5 |
| Partially neutralized polyacrylic acid (NP-700) | 5 |
| Partially neutralized polyacrylic acid (NP-800) | 5 |
| Tartaric acid | 1.3 |
| Dihydroxy aluminum acetate | 0.2 |
| Macrogol 400 | 20 |
| Normal saline solution | Appropriate amount |
| Total | 100 |

One (1) g of indomethacin was dissolved in the oily phase of Table 4 to prepare a pad containing indomethacin. An aluminum electrode was attached to the pad and a donor having a circular form shown in FIG. 3 was prepared. In the meantime, an aluminum electrode was attached to a pad (not containing indomethacin) of Table 4 to obtain a receptor having a shape of FIG. 3.

The invention claimed is:

1. An iontophoretic therapy for treating breast cancer and/or mastitis, wherein the therapy comprises applying a donor which contains an anticancer agent as an active ingredient on a nipple part and topically administering the active ingredient from the nipple part into a mammary gland by applying electric potential.

2. The therapy according to claim 1, wherein the anticancer agent is cyclophosphamide or fluorouracil.

3. The therapy according to claim 1, wherein the donor comprises an electrode and a pad containing the active ingredient.

4. The therapy according to claim 1, wherein the therapy comprises applying a receptor on the breast part.

5. The therapy according to claim 3, wherein the therapy comprises applying the donor on the nipple part and applying the receptor on the breast part and the donor has a size to cover the nipple and the receptor has a size to cover at least an affected part of the breast.

6. The therapy according to claim 5, wherein the receptor is in a form of a disk or an oval disk which covers up the whole breast except the nipple part.

7. The therapy according to claim 4, wherein the therapy comprises applying the donor on the nipple part and applying the receptor on the breast part and the donor has a size to cover the nipple and the receptor has a size to cover at least an affected part of the breast.

8. The therapy according to claim 2, wherein the donor comprises an electrode and a pad containing the active ingredient.

9. The therapy according to claim 2, wherein the therapy comprises applying a receptor on the breast part.

10. The therapy according to claim 3, wherein the therapy comprises applying a receptor on the breast part.

* * * * *